(12) United States Patent
Kim et al.

(10) Patent No.: US 9,782,088 B2
(45) Date of Patent: Oct. 10, 2017

(54) PULSE MEASURING DEVICE AND METHOD OF PULSE MEASUREMENT THEREWITH

(71) Applicant: KOREA INSTITUTE OF ORIENTAL MEDICINE, Daejeon (KR)

(72) Inventors: Young Min Kim, Daejeon (KR); Jae Uk Kim, Daejeon (KR); Young Ju Jeon, Daejeon (KR); Jong Yeol Kim, Daejeon (KR); Si Woo Lee, Jeonju-si (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 428 days.

(21) Appl. No.: 14/408,543

(22) PCT Filed: Jul. 2, 2013

(86) PCT No.: PCT/KR2013/005848
§ 371 (c)(1),
(2) Date: Dec. 16, 2014

(87) PCT Pub. No.: WO2014/014214
PCT Pub. Date: Jan. 23, 2014

(65) Prior Publication Data
US 2015/0190065 A1   Jul. 9, 2015

(30) Foreign Application Priority Data

Jul. 18, 2012  (KR) ........................ 10-2012-0078154

(51) Int. Cl.
*A61B 5/02* (2006.01)
*A61B 5/024* (2006.01)
*A61B 5/00* (2006.01)

(52) U.S. Cl.
CPC .......... *A61B 5/02427* (2013.01); *A61B 5/024* (2013.01); *A61B 5/4854* (2013.01);
(Continued)

(58) Field of Classification Search
CPC ... A61B 5/024; A61B 5/02427; A61B 5/4854; A61B 5/6887; A61B 5/6824;
(Continued)

(56) References Cited

U.S. PATENT DOCUMENTS

2011/0257543 A1* 10/2011 Jeon ........................ A61B 5/021
600/502
2012/0190981 A1* 7/2012 Harris .................... A61B 34/30
600/439

FOREIGN PATENT DOCUMENTS

KR    10-2002-0096224 A    12/2002
KR    10-2003-0069743 A    8/2003
(Continued)

*Primary Examiner* — Mallika D Fairchild
(74) *Attorney, Agent, or Firm* — McDermott, Will & Emery LLP (57) ABSTRACT

A pulse measuring device according to one embodiment of the present invention comprises: a measuring unit which is capable of spherical movement with multiple degrees of freedom; and a movement unit on which the measuring unit is mounted, and which has a spherical movement part for moving the measuring unit spherically with multiple degrees of freedom while also having a linear movement structure for moving the measuring unit linearly with multiple degrees of freedom. The measuring unit comprises: a unit body which is coupled so as to be able to rotate relative to an end part of the movement unit; a linking part which is coupled to a lower end part of the unit body and is able to rotate relative to the unit body; and a sensor part which is equipped with a pulse diagnosis sensor.

13 Claims, 11 Drawing Sheets

(52) U.S. Cl.
 CPC .......... *A61B 5/6824* (2013.01); *A61B 5/6844* (2013.01); *A61B 5/6887* (2013.01)

(58) Field of Classification Search
 CPC ..... A61B 5/6831; A61B 5/6844; A61B 5/702; A61B 5/021; A61B 5/02; A61B 5/022
 See application file for complete search history.

(56) References Cited

FOREIGN PATENT DOCUMENTS

| | | |
|---|---|---|
| KR | 10-2010-0101868 A | 9/2010 |
| KR | 10-1033001 B1 | 4/2011 |

\* cited by examiner

PULSE MEASURING DEVICE AND METHOD OF PULSE MEASUREMENT THEREWITH

TECHNICAL FIELD

Embodiments of the present invention relate to a pulse measuring device and a pulse measuring method thereof, more particularly, to a pulse measuring device and a pulse measuring method thereof that may adjust a position of a measuring unit including a pulse diagnosis sensor to a precise pulse position by linearly moving a movement unit with multiple degrees of freedom and spherically moving the measuring unit with multiple degrees of freedom.

BACKGROUND ART

In oriental medicine, a pulse diagnosis may be used to diagnose a disease of an examinee by measuring a pulse at specific positions on an artery located inside a wrist, the specific positions such as Cun, Guan, and Chi, for example. The pulse diagnosis is to verify whether twelve organs function properly by verifying a balance between Qi and Xie flowing through a human body. In general, a physical condition may be examined by sensing pulse strength and weakness, pulse frequency, and the like while placing three fingers to be in contact with the three points, Cun, Guan, and Chi.

However, long term experience may be required to attain proficiency in the pulse diagnosis. In addition, since a case of a patient or a seriousness of a disease is determined based on a sensation in fingers, systemization of many states observed depending on physical constitutions of patients is difficult, and a possibility of misdiagnosis exists. Further, although objective data is required to prepare a prescription based on a physical constitution of a patient, materialization of such data may be difficult.

To solve such issues, pulse measuring devices configured to be mechanically driven to measure a pulse have been developed and are actually in use.

However, in the existing pulse measuring devices, a measurement time may increase due to an inconvenience in indicating a pulse position, and inaccurate initialization of the pulse position may impede obtainment of a precise pulse wave. Further, the pulse measuring devices have structures having difficulties in pressurizing a skin surface in a vertical direction. Thus, during measurement, a slip may occur and fixing the fingers on a radial artery may be difficult. In addition, when the skin surface is pressurized deeply, pain may occur.

Accordingly, there is a demand for development of a pulse measuring device that may dispose a pulse wave sensor exactly at a pulse position, and pressurize the skin in a vertical direction thereby preventing an occurrence of a slip, and the like.

DISCLOSURE OF INVENTION

Technical Goals

An aspect of the present invention provides a pulse measuring device and a pulse measuring method thereof that may adjust a position of a measuring unit including a pulse diagnosis sensor to a precise pulse position by linearly moving a movement unit with multiple degrees of freedom and spherically moving the measuring unit with multiple degrees of freedom, and dispose the measuring unit to pressurize a surface of the skin including the pulse position in a vertical direction, thereby performing a pulse diagnosis accurately.

Another aspect of the present invention provides a pulse measuring device and a pulse measuring method thereof that may prevent a slip of a measuring unit with respect to the skin by enabling the measuring unit to pressurize the skin including a pulse position in a vertical direction, and prevent excessive pain to an examinee through appropriate pressurization.

Technical Solutions

According to an aspect of the present invention, there is provided a pulse measuring device including a measuring unit configured to move spherically with multiple degrees of freedom, and a movement unit on which the measuring unit is provided, the movement unit including a spherical movement portion configured to spherically move the measuring unit with multiple degrees of freedom while having a linear movement structure to linearly move the measuring unit with multiple degrees of freedom. The measuring unit may include a unit body rotatably connected to one end portion of the movement unit, a connecting portion connected to a lower end portion of the unit body, and configured to rotate with respect to the unit body, and a sensor portion rotatably connected to the connecting portion, the sensor portion including a pulse diagnosis sensor. When the pulse diagnosis sensor is in contact with a pulse position, a position of the measuring unit may be adjusted to enable the measuring unit to pressurize the pulse position in a vertical direction by spherically moving the measuring unit with multiple degrees of freedom using the spherical movement portion. In addition, the measuring unit may be disposed to pressurize a surface of the skin including the pulse position in a vertical direction, thereby performing a pulse diagnosis accurately.

The measuring unit may be configured to move spherically with three degrees of freedom, and the movement unit may be configured to move linearly with three degrees of freedom.

The unit body may include a body member, a pair of parallel members disposed to be parallel from the body member toward a lower side, and a pair of extending members configured to extend from the body member toward both sides. The connecting portion may be rotatably connected to the pair of parallel members.

A pair of light emitting portions may be disposed at the pair of extending members to emit lights toward the skin, respectively, and an initial position of the measuring unit may be set by matching the pulse position and the pair of lights emitted from the pair of light emitting portions.

The connecting portion may include a connecting bar to which the sensor portion is rotatably connected, and a pair of joint members connected to both sides of the connecting bar, respectively, and connected to the pair of parallel members, respectively, the pair of joint members including two joints configured to enable the pair of joint members to perform bending motions with respect to the pair of parallel members.

The sensor portion may include a sensor housing tiltably connected to the connecting portion, the sensor housing on which the pulse diagnosis sensor is provided at a lower end portion, and a tilting sensor configured to measure a gradient of the pulse diagnosis sensor with respect to the pulse position.

The sensor housing may include a first joint portion tiltably connected to the connecting portion, and a second joint portion linked to the first joint portion. When adjusting the position of the measuring unit to enable the measuring unit to pressurize the pulse position in the vertical direction, the second joint portion may be configured to perform a bending motion with respect to the first joint portion.

The movement unit may include a supporting frame supported on a supporting surface, the supporting frame including a first rail, a first movement frame configured to move linearly along the first rail in one direction, the first movement frame including a second rail in a direction perpendicular to the one direction, a second movement frame configured to move linearly along the second rail, the second movement frame including a third rail in a vertical direction, and a third movement frame configured to move linearly along the third rail in the vertical direction, the third movement frame with one end portion at which the spherical movement portion is provided.

The spherical movement portion may include a pair of link members having a joint structure enabling a bending motion, the pair of link members configured to spherically move the measuring unit with three degrees of freedom based on the bending motion.

The pulse measuring device may further include a photographing unit configured to photograph a position of the pulse diagnosis sensor with respect to the pulse position, and a processing unit configured to receive and process pulse diagnosis information obtained by the pulse diagnosis sensor.

According to another aspect of the present invention, there is also provided a pulse measuring method of a pulse measuring device including a measuring unit including a pulse diagnosis sensor configured to sense a pulse wave at a pulse position of the skin, the measuring unit configured to move spherically with multiple degrees of freedom, and a movement unit on which the measuring unit is provided, the movement unit including a spherical movement portion configured to spherically move the measuring unit with multiple degrees of freedom while having a linear movement structure to linearly move the measuring unit with multiple degrees of freedom, the method including indicating a pulse position on a surface of the skin, setting an initial position of the measuring unit with respect to the pulse position to match the pulse position and a position of a light emitted from a light emitting portion provided in the measuring unit, moving the measuring unit to dispose the pulse diagnosis sensor to be in contact with the pulse position by linearly moving the movement unit with multiple degrees of freedom, and readjusting a position of the measuring unit to enable the measuring unit to pressurize the surface of the skin including the pulse position in a vertical direction through spherical movement with multiple degrees of freedom. Through the foregoing configuration, the position of the measuring unit including the pulse diagnosis sensor may be adjusted to a precise pulse position by linearly moving the movement unit with multiple degrees of freedom and spherically moving the measuring unit with multiple degrees of freedom. Further, the measuring unit may be disposed to pressurize the surface of the skin including the pulse position in a vertical direction, thereby performing a pulse diagnosis accurately.

The readjusting may include measuring a gradient of the pulse diagnosis sensor with respect to the surface of the skin, and adjusting a pressurization direction of the measuring unit to match the pressurization direction and the measured gradient.

The measuring unit may include a unit body rotatably connected to the movement unit, a connecting portion configured to rotate with respect to the unit body, and a sensor portion configured to tilt with respect to the connecting portion, the sensor portion including the pulse diagnosis sensor, and the adjusting may include tilting the sensor portion with respect to the connecting portion to dispose the pulse diagnosis sensor to be in surface contact with the surface of the skin, bending the connecting portion, and matching an axial direction of the unit body and an axial direction of the sensor portion.

The setting may include performing photographing using a photographing unit provided in the pulse measuring device to verify whether the pulse position and the position of the light emitted from the light emitting portion match.

Advantageous Effects

According to embodiments of the present invention, a position of a measuring unit including a pulse diagnosis sensor may be adjusted to a precise pulse position by linearly moving a movement unit with multiple degrees of freedom and spherically moving the measuring unit with multiple degrees of freedom, and the measuring unit may be disposed to pressurize a surface of the skin including the pulse position in a vertical direction, whereby a pulse diagnosis may be preformed accurately.

According to embodiments of the present invention, a slip of a measuring unit with respect to the skin may be prevented by enabling the measuring unit to pressurize the skin including a pulse position in a vertical direction, and excessive pain to an examinee may be prevented through appropriate pressurization.

BEST MODE FOR CARRYING OUT THE INVENTION

Hereinafter, a configuration and an operation according to an embodiment of the present invention will be described with reference to the accompanying drawings. The following description will be one of aspects of the present invention and constitute a portion of the detailed description of the present invention.

However, when describing the present invention, detailed description related to a known function or configuration will be omitted for clarity.

Figure 1:
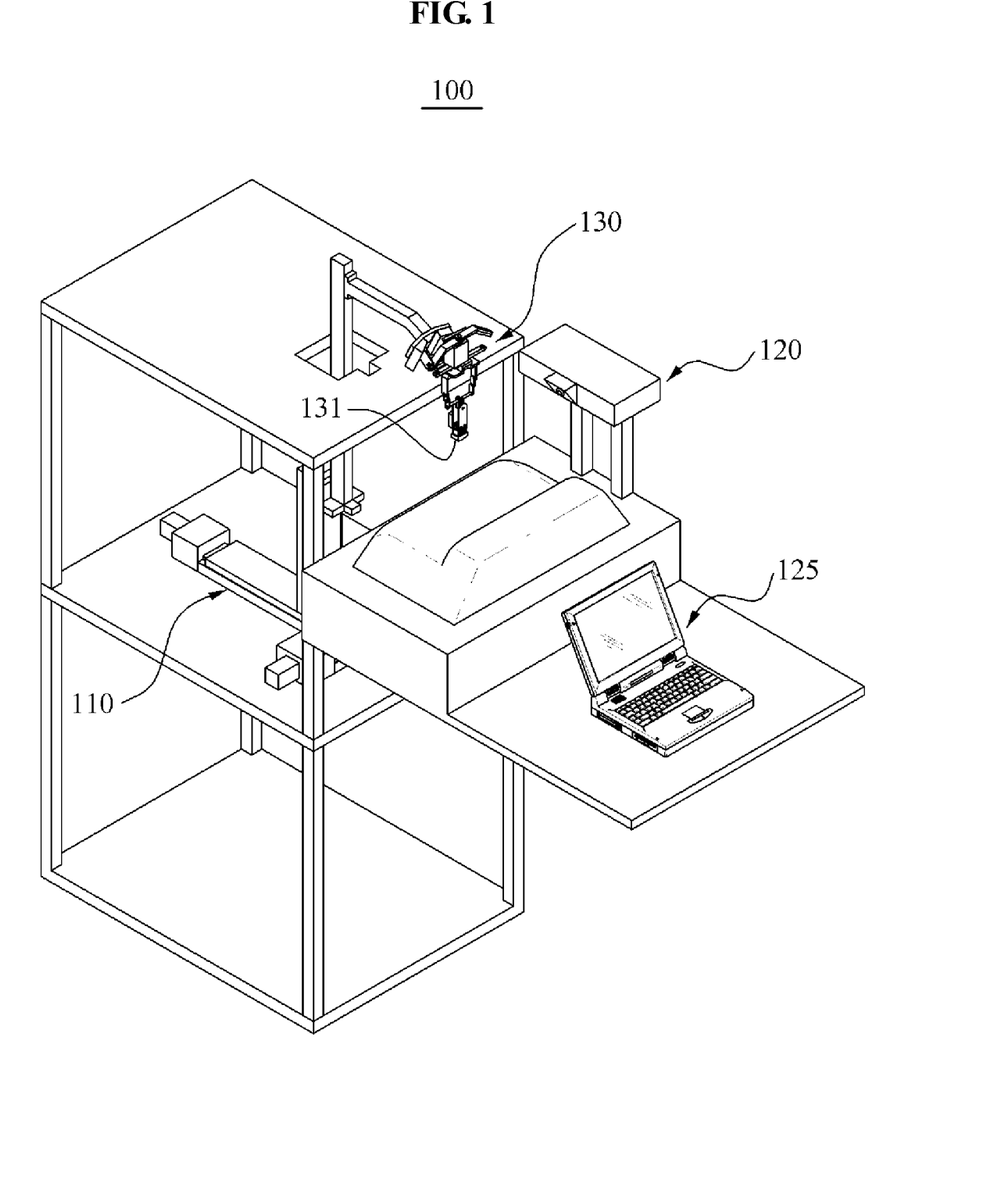
FIG. 1 is a perspective view illustrating a configuration of a pulse measuring device according to an embodiment of the present invention.
Figure 2:
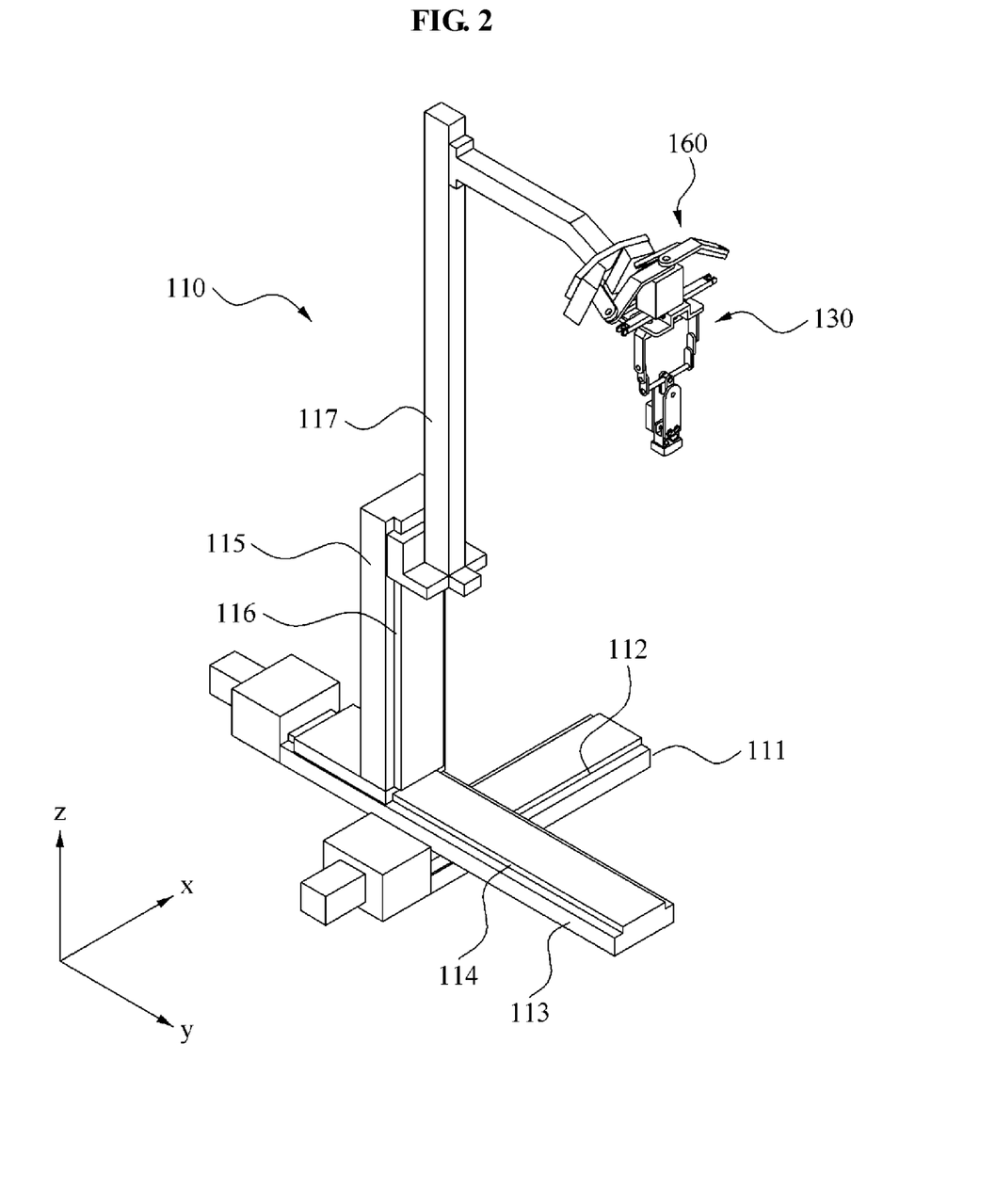
FIG. 2 is a perspective view illustrating a measuring unit and a movement unit of FIG. 1.
Figure 3:
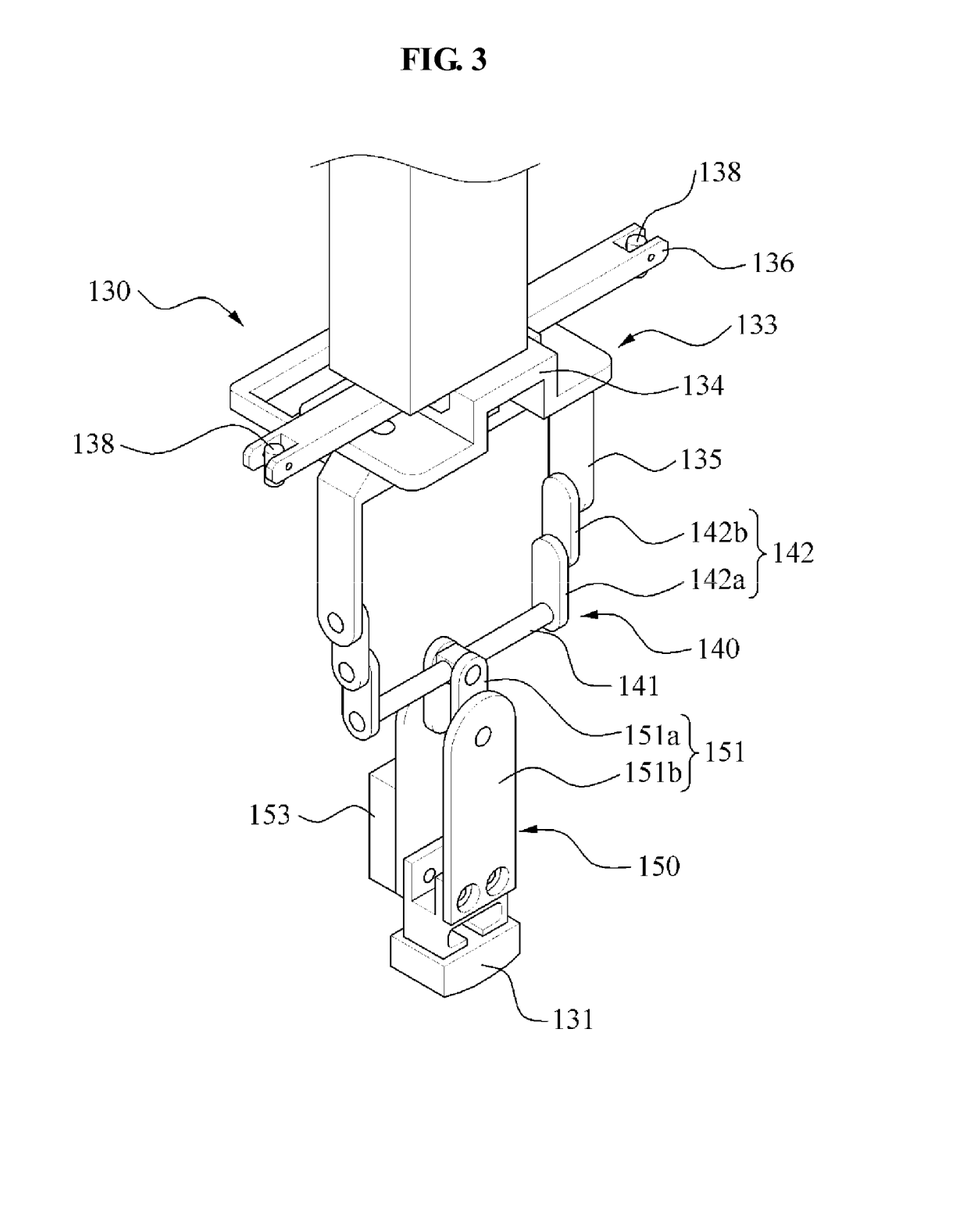
FIG. 3 is a perspective view illustrating the measuring unit of FIG. 2.
Figure 4:
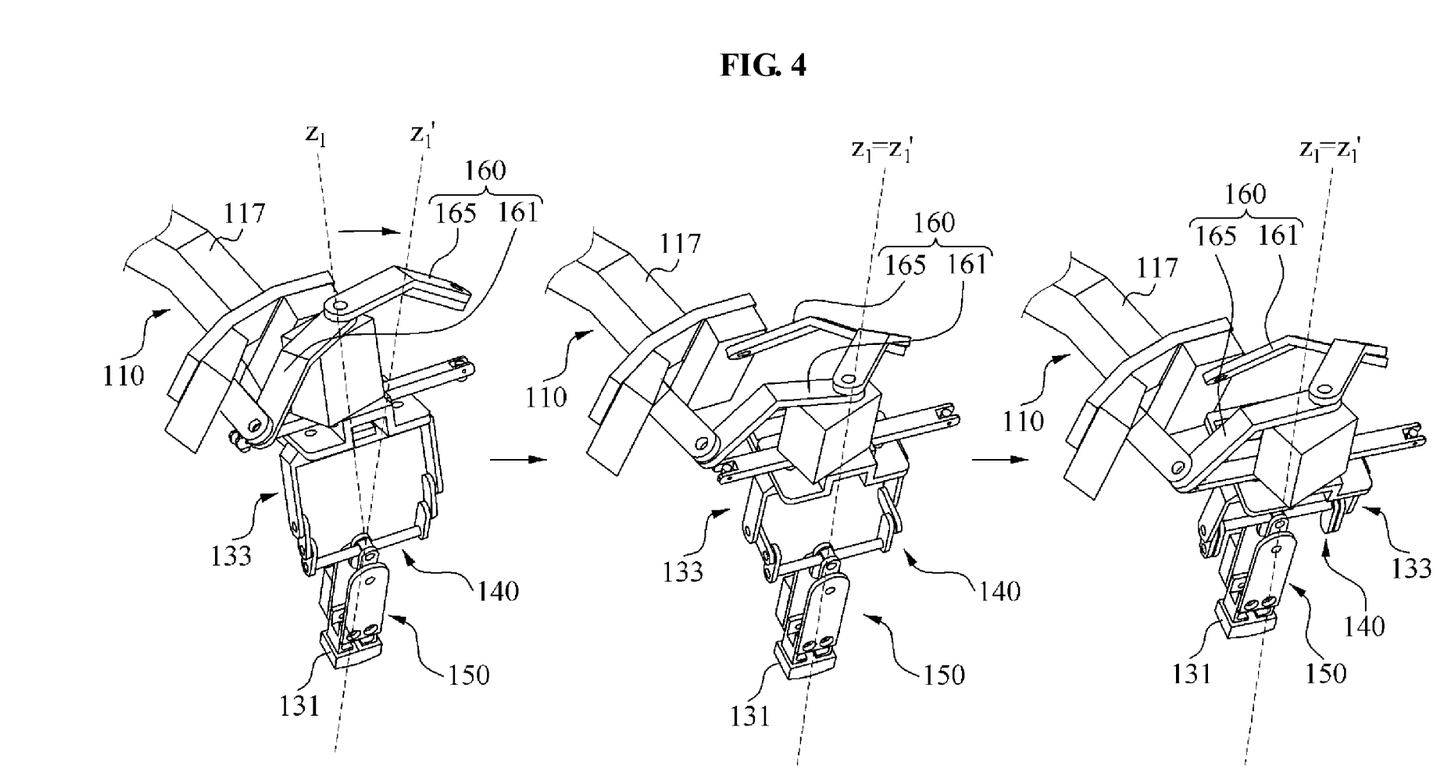
FIG. 4 is a view illustrating an operation of spherically moving the measuring unit using a spherical movement portion of the movement unit of FIG. 2.

FIG. 1 is a perspective view illustrating a configuration of a pulse measuring device according to an embodiment of the present invention, FIG. 2 is a perspective view illustrating a measuring unit and a movement unit of FIG. 1, FIG. 3 is a perspective view illustrating the measuring unit of FIG. 2, and FIG. 4 is a view illustrating an operation of spherically moving the measuring unit using a spherical movement portion of the movement unit of FIG. 2.

Referring to FIG. 1, a pulse measuring device 100 according to an embodiment of the present invention may include a measuring unit 130 including a pulse diagnosis sensor 131 configured to be in direct contact with a pulse position P of the skin (refer to FIG. 6) to perform a pulse diagnosis, the measuring unit 130 configured to move spherically with three degrees of freedom (3 DoF), a movement unit 110 on which the measuring unit 130 is disposed, the movement unit 110 configured to linearly move the measuring unit 130 with 3 DoF, a photographing unit 120 configured to photograph a position of the pulse diagnosis sensor 131 with respect to the skin, and a processing unit 125 configured to receive and process pulse diagnosis information obtained by the pulse diagnosis sensor 131. In the present embodiment, the processing unit 125 may include a personal computer (PC).

The measuring unit 130 may move spherically with 3 DoF to pressurize the skin in a vertical direction when the pulse diagnosis sensor 131 is disposed to be in contact with the pulse position of the skin.

By the foregoing configuration, the pulse diagnosis sensor 131 may be disposed at a precise position, and a slip of the pulse diagnosis sensor 131 with respect to the skin may be prevented during pressurization. Thus, measurement may be performed accurately.

A configuration of the movement unit 110 will be described. As shown in FIG. 2, the movement unit 110 may include a supporting frame 111, a first movement frame 113 connected to the supporting frame 111 to move linearly, a second movement frame 115 connected to the first movement frame 113 to move linearly, and a third movement frame 117 connected to the second movement frame 115 to move linearly. The measuring unit 130 may be disposed at an end portion of the third movement frame 117.

By the foregoing configuration, the movement unit 110 may have a structure to move linearly with 3 DoF. In detail, a first rail 112 may be provided on the supporting frame 111 in one direction, for example, an x-axial direction. The first movement frame 113 may move linearly along the first rail 112 in the one direction.

A second rail 114 may be provided on the first movement frame 113 in a direction perpendicular to the one direction, for example, a y-axial direction. The second movement frame 115 may move linearly along the second rail 114. Further, a third rail 116 may be provided on the second movement frame 115 in a vertical direction, for example, a z-axial direction. The third movement frame 117 may move linearly along the third rail 116.

Thus, the measuring unit 130 connected to the end portion of the third movement frame 117 may move accurately to a desired position, for example, above the pulse position P by a 3 DoF linear movement structure of the movement unit 110.

The movement unit 110 may further include a spherical movement portion 160 configured to spherically move the measuring unit 130 with 3 DoF to enable the measuring unit 130 to pressurize the surface of the skin including the pulse position P in a vertical direction. The spherical movement portion 160 will be described in detail along with the configuration of the measuring unit 130 after the measuring unit 130 is described.

As shown in FIG. 3, the measuring unit 130 may be connected to the end portion of the movement unit 110, and be in contact with the pulse position P of the skin to directly perform a pulse diagnosis. The measuring unit 130 may accurately verify the pulse position P. In addition, the measuring unit 130 may have a 3 DoF spherical movement structure that may dispose the pulse diagnosis sensor 131 at the precise pulse position P and pressurize the surface at the pulse position P in a vertical direction.

In detail, the measuring unit 130 may include a unit body 133 rotatably connected to one end portion of the movement unit 110, for example, the end portion 117a of the third movement frame 117, a connecting portion 140 connected to a lower end portion of the unit body 133 and configured to rotate with respect to the unit body 133, and a sensor portion 150 rotatably connected to the connecting portion 140. The pulse diagnosis sensor 131 may be provided on the sensor portion 150.

The unit body 133, the connecting portion 140, and the sensor portion 150 may have structures rotatable with respect to the movement unit 110, the unit body 133, and the connecting portion 140, respectively. Thus, the pulse diagnosis sensor 131 provided on the sensor portion 150 may move spherically with 3 DoF, thereby being disposed in a desired position at a precise angle.

The unit body 133 may include a body member 134 configured to form a basic skeleton, a pair of parallel members 135 disposed to be parallel from the body member 134 toward a lower side, and a pair of extending members 136 configured to extend from the body member 134 toward both sides. A pair of light emitting portions 138 may be disposed at the pair of extending members 136 to emit lights, for example, laser beams, toward the skin to be in contact to measure a pulse, respectively.

The body member 134 may be rotatably connected to the end portion 117a of the third movement frame 117 of the movement unit 110. Although FIGS. 2 and 3 illustrate the third movement frame 117 and the body member 134 being connected by a single end portion, for example, the connecting member 117a, the third movement frame 117 and the body member 134 may be connected by a pair of connecting members (not shown). By interoperation between the pair of connecting members, the body member 134 may rotate with respect to the third movement frame 117, and a position of the body member 134 may be adjusted at a desired angle.

The pair of parallel members 135 may be portions to which the connecting portion 140 is connected. The connecting portion 140 may have a bending structure with respect to the parallel members 135.

The light emitting portions 138 may be disposed on outer sides of the extending members 136, respectively. The light emitting portions 138 may emit laser beams toward the skin (refer to FIG. 6). Prior to pulse measurement, the pulse position P may be indicated on the skin. The measuring unit 130 may be disposed to match the pulse position P and the laser beams emitted from the pair of light emitting portions 138 by driving the movement unit 110, whereby an initial position of the pulse diagnosis sensor 131 may be set accurately.

The connecting portion 140 may be a portion configured to adjust a position with respect to the unit body 133 through a bending motion. The connecting portion 140 may include a connecting bar 141 to which the sensor portion 150 is rotatably connected, and a pair of joint members 142 connected to both sides of the connecting bar 141, respectively. The pair of joint members 142 may include two joints 142a and 142b configured to enable the pair of joint members 142 to perform bending motions with respect to the parallel members 135, respectively.

By the foregoing structure of the connecting portion 140, the pulse diagnosis sensor 131 of the sensor portion 150 may be disposed to be in contact with the pulse position P and pressurize the pulse position P in a vertical direction. In this example, the joint members 142 may be bent and thus, force may be transmitted more efficiently.

The sensor portion 150 may include a sensor housing 151 tiltably connected to the connecting bar 141, the pulse diagnosis sensor 131 connected to a lower end portion of the sensor housing 151, and a tilting sensor 153 configured to measure a gradient of the pulse diagnosis sensor 131 with respect to the skin.

Here, similar to the structure of the connecting portion 141, the sensor housing 151 may also have a joint structure. In detail, the sensor housing 151 may include a first joint portion 151a connected to the connecting bar 141, and a second joint portion 151b linked to the first joint portion 151a. Thus, the sensor housing 151 may perform a bending motion, and adjust a position and an angle thereof appropriately.

As described above, to prevent a slip of the pulse diagnosis sensor 131 with respect to the skin and transmit a precise force, disposing the pulse diagnosis sensor 131 in a vertical direction with respect to the pulse position P and applying the force in the vertical direction may be significant. To achieve this, the tilting sensor 153 may be disposed on the sensor housing 151 to measure an angle of the pulse diagnosis sensor 131 with respect to the skin. Based on information measured by the tilting sensor 153, an angle of the sensor portion 150 may be adjusted, an angle of the unit body 133 with respect to the sensor portion 150 may be adjusted for matching, and the bending motions of the connecting portion 140 may be performed, whereby the measuring unit 130 may be disposed in the vertical direction with respect to the surface of the skin including the pulse position P.

However, although not described in the present embodiment, driving portions (not shown) may be provided separately to drive the sensor portion 150 and the connecting portion 140. By separately driving the driving portions, the measuring unit 130 may be driven minutely.

As described above, the spherical movement portion 160 may be provided in the movement unit 110 to spherically move the measuring unit 130. As shown in FIG. 4, the spherical movement portion 160 may include a pair of link members 161 and 165 having a joint structure enabling a bending motion. The pair of link members 161 and 165 may spherically move the measuring unit 130 with 3 DoF based on the bending motion.

In detail, one of both ends of each of the pair of link members 161 and 165 may be connected to the third movement frame 117, and the other end thereof may be connected to an upper end portion of the measuring unit 130. Thus, the measuring unit 130 may move spherically with 3 DoF based on the bending motions of the pair of the link members 161 and 165 that shrink or expand based on connected portions of joints. In this example, the pair of link members 161 and 165 may be driven by a separate driving portion (not shown).

As shown sequentially in FIG. 4, the sensor portion 150 of the measuring unit 130 on which the pulse diagnosis sensor 131 is provided may rotate by the connecting portion 140 to be disposed in a vertical direction with respect to the surface of the skin when in contact with the surface of the skin. In this example, a gradient direction of the sensor portion 150 and a gradient direction of the unit body 133 may need to match. By expanding the pair of link members 161 and 165, the unit body 133 may move spherically and thus, the direction of the measuring unit 130 with respect to the surface of the skin may be adjusted to be a vertical direction.

However, after the gradient directions of the sensor portion 150 and the unit body 133 match (refer to the middle image of FIG. 4), the connecting portion 140 may need to shrink as shown in the right image of FIG. 4. The shrinkage of the connecting portion 140 may be performed by a separate driving portion configured to drive the connecting portion 140 to be bent, as described above.

Hereinafter, a pulse measuring method of a pulse measuring device configured as described above according to an embodiment of the present invention will be described with reference to the drawings.

Figure 5:
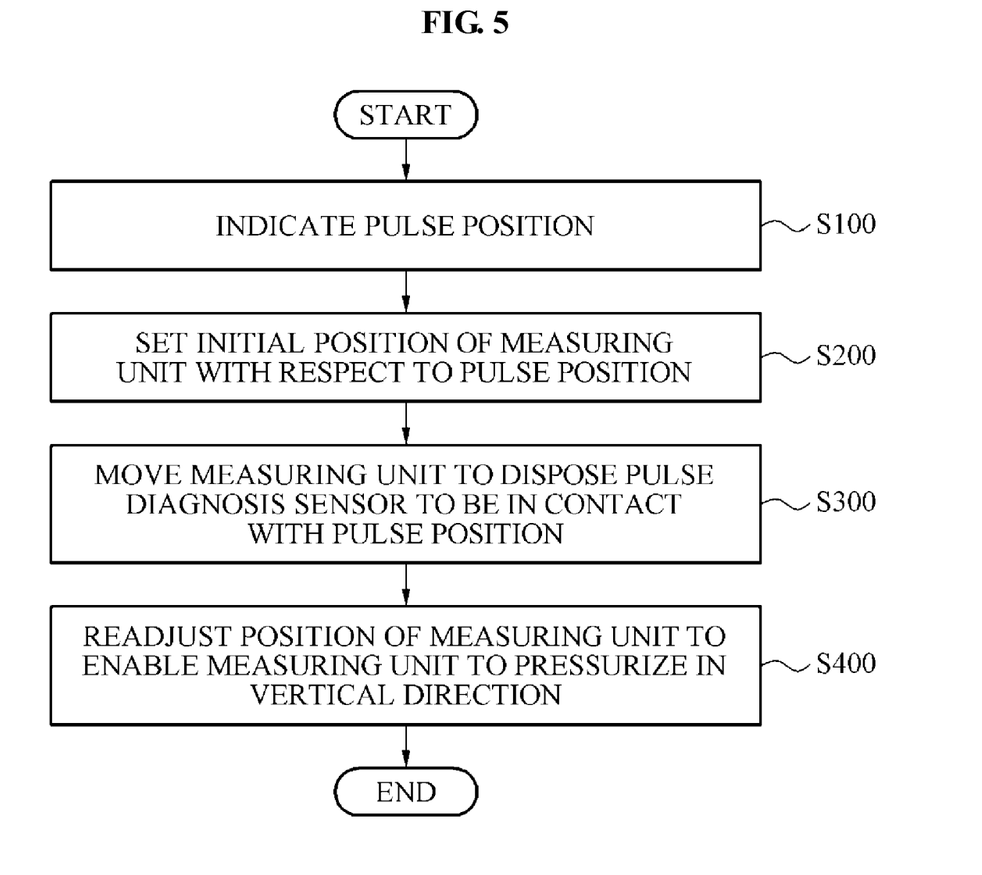
FIG. 5 is a flowchart illustrating a pulse measuring method of a pulse measuring device according to an embodiment of the present invention.
Figure 6:
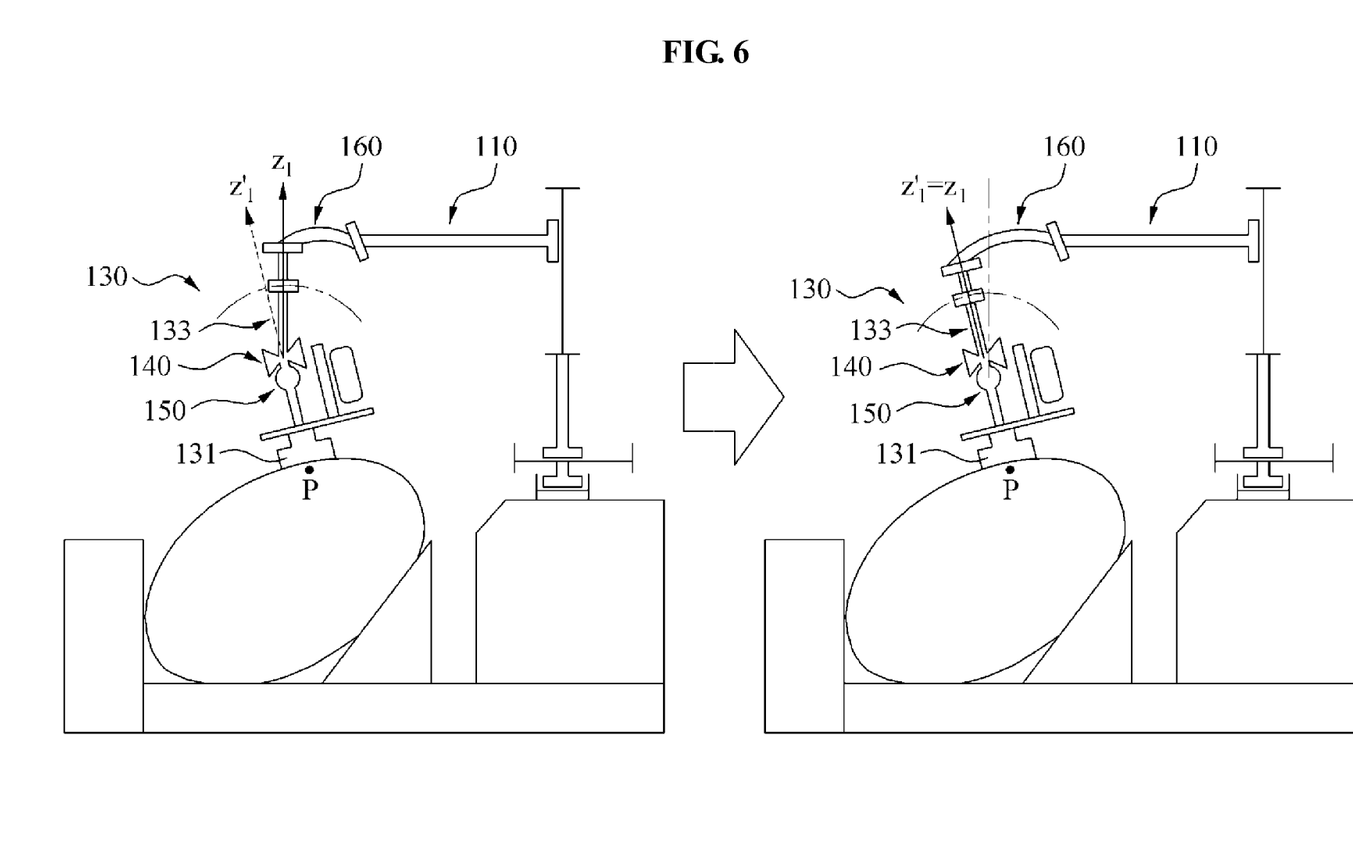
FIG. 6 is a view illustrating a mechanism of the pulse measuring method of FIG. 5.
Figure 7:
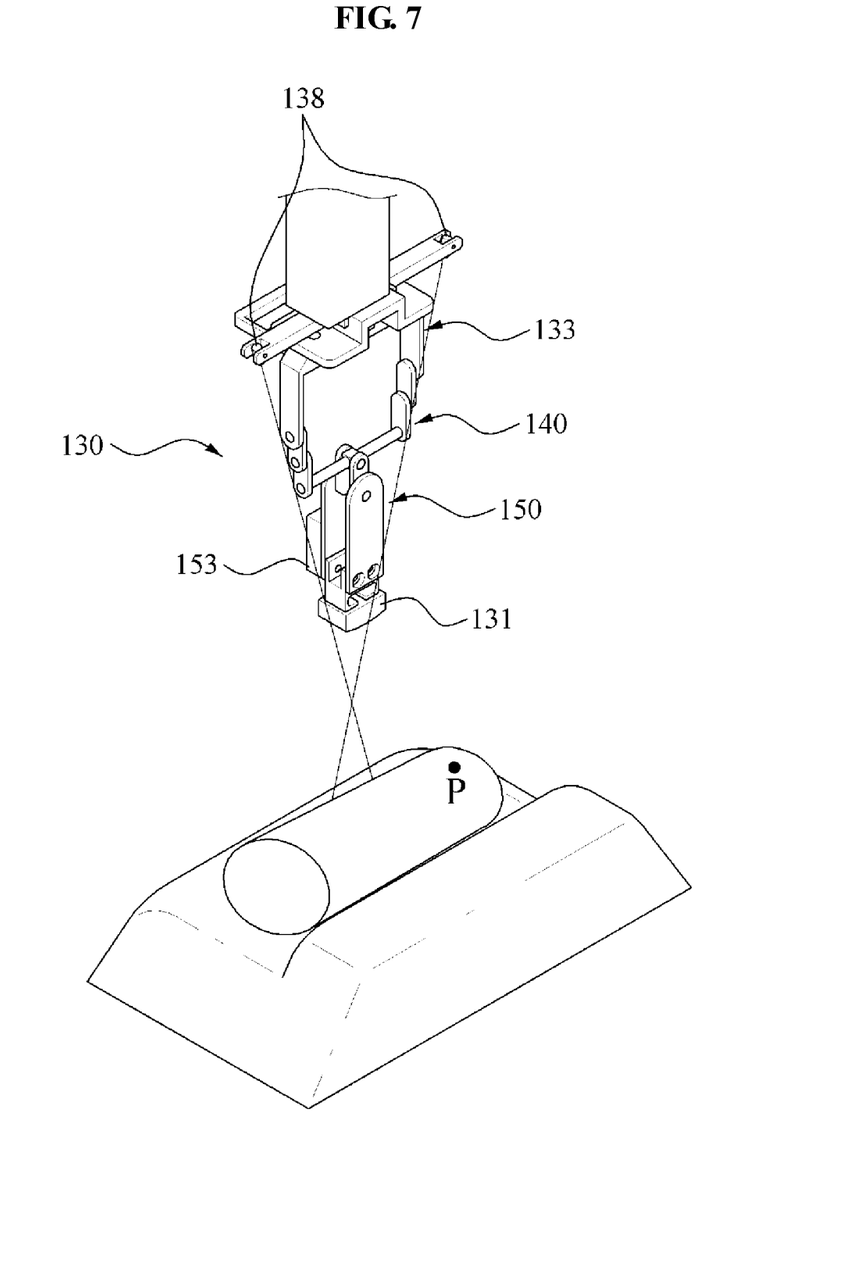
FIG. 7 is a perspective view illustrating an operation of indicating a pulse position in the pulse measuring method of FIG. 5.
Figure 8:
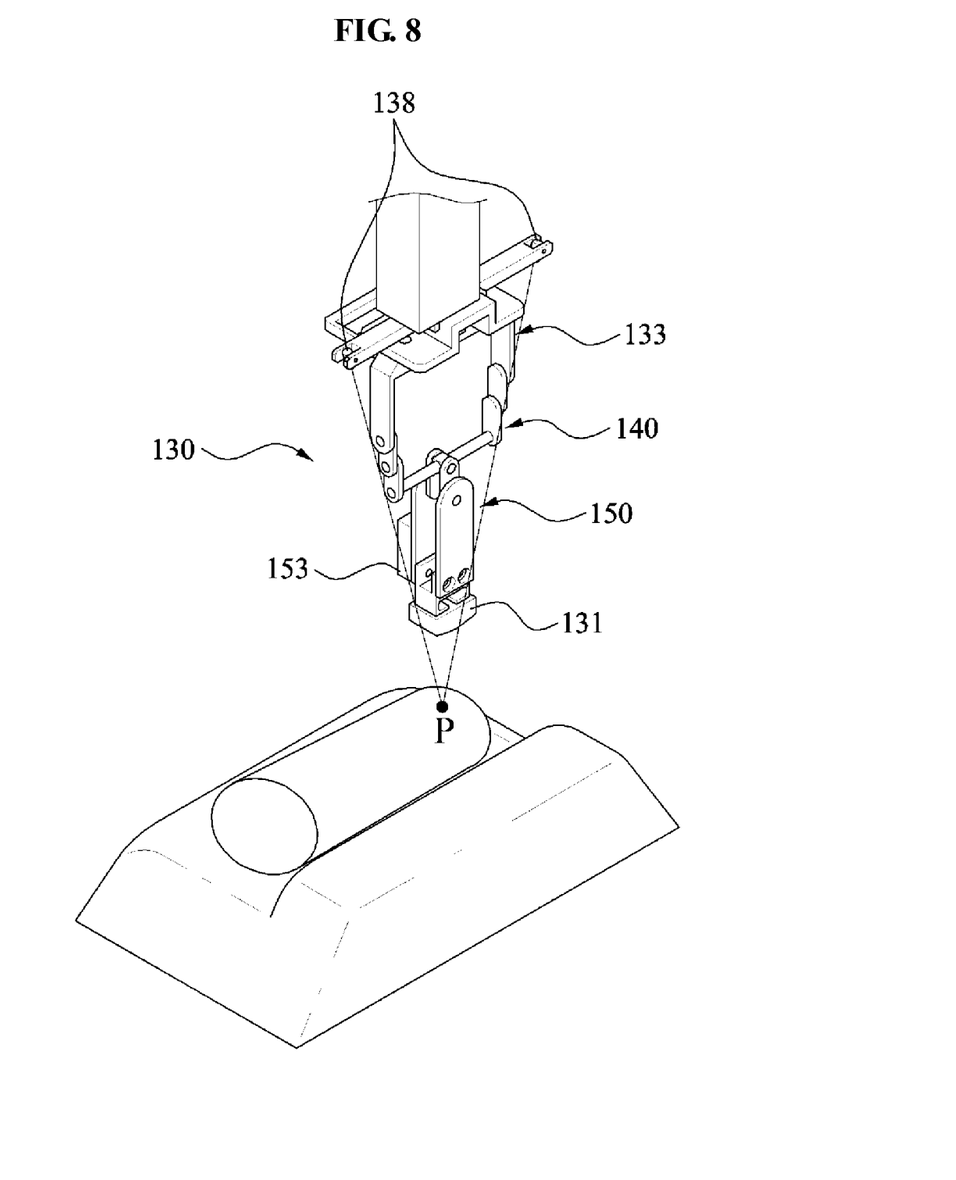
FIG. 8 is a perspective view illustrating an operation of setting an initial position of a measuring unit in the pulse measuring method of FIG. 5.
Figure 9:
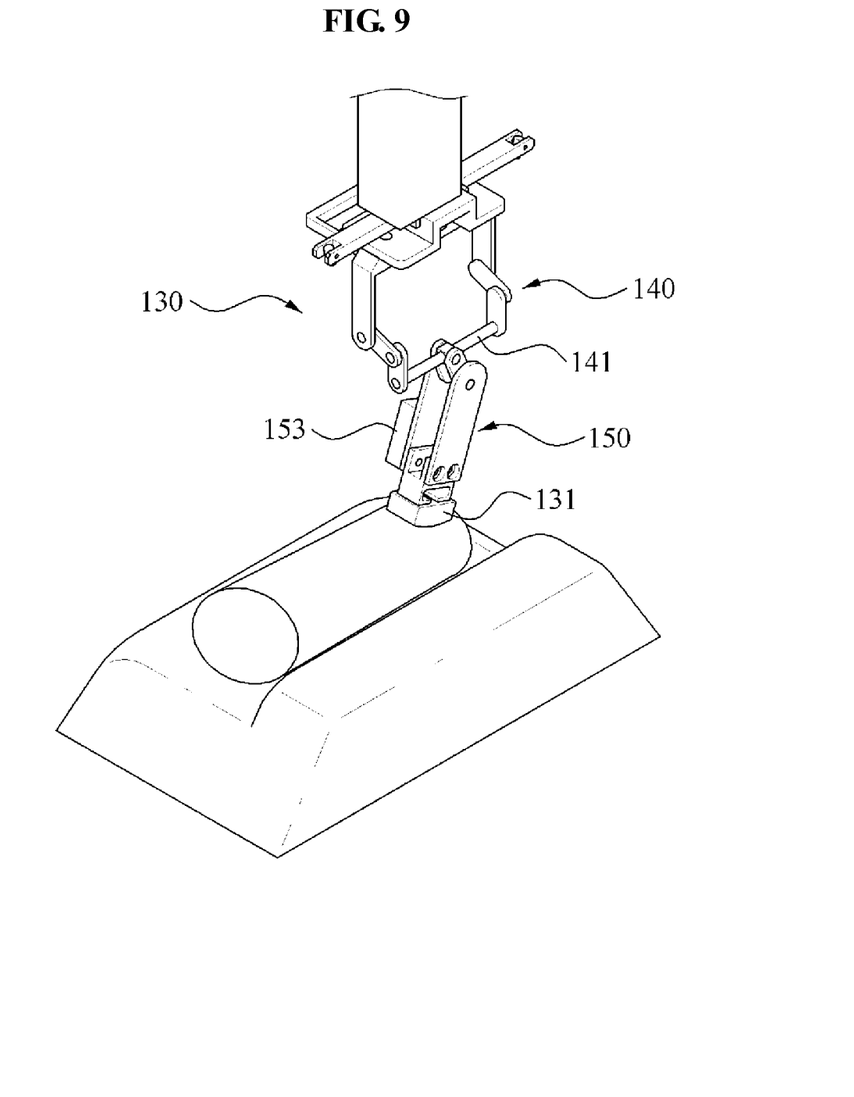
FIG. 9 is a perspective view illustrating an operation of moving a measuring unit in the pulse measuring method of FIG. 5.
Figure 10:
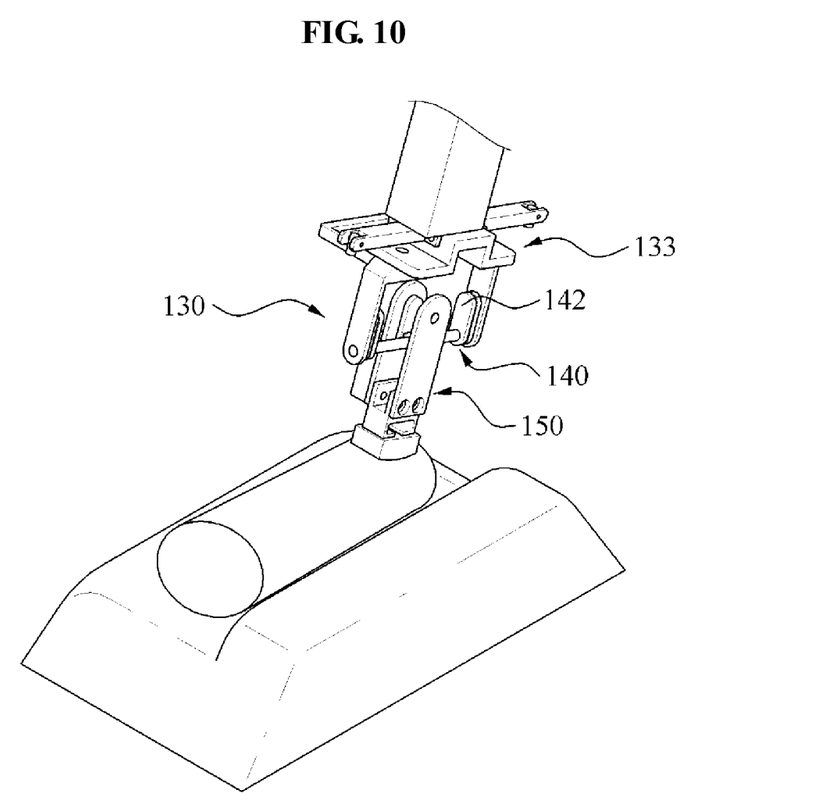
FIG. 10 is a perspective view illustrating an operation of readjusting a position of a measuring unit in the pulse measuring method of FIG. 5.
Figure 11:
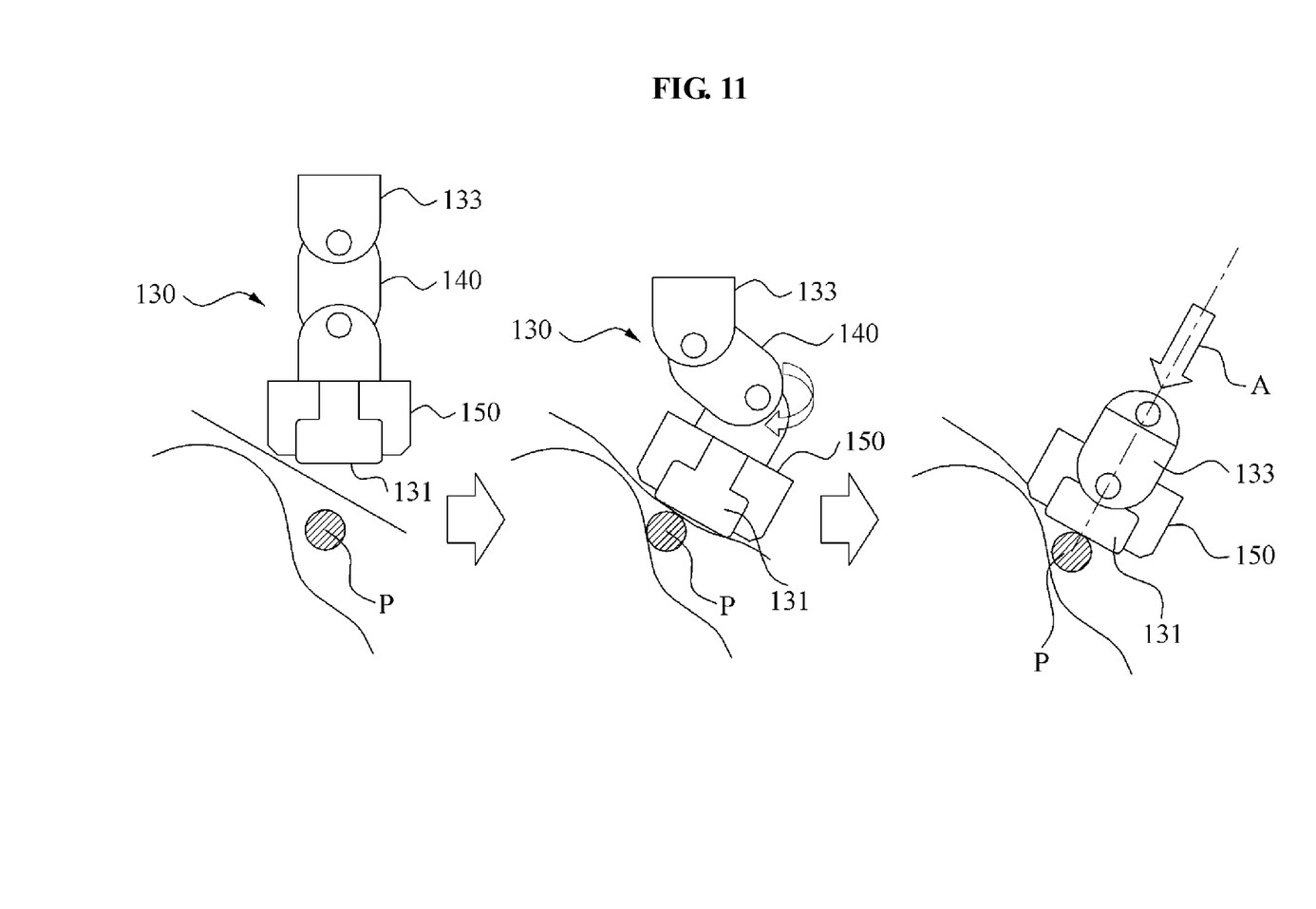
FIG. 11 is a view illustrating the operations of FIGS. 8 through 10 sequentially.

FIG. 5 is a flowchart illustrating a pulse measuring method of a pulse measuring device according to an embodiment of the present invention, FIG. 6 is a view illustrating a mechanism of the pulse measuring method of FIG. 5, FIG. 7 is a perspective view illustrating an operation of indicating a pulse position in the pulse measuring method of FIG. 5, FIG. 8 is a perspective view illustrating an operation of setting an initial position of a measuring unit in the pulse measuring method of FIG. 5, FIG. 9 is a perspective view illustrating an operation of moving the measuring unit in the pulse measuring method of FIG. 5, FIG. 10 is a perspective view illustrating an operation of readjusting a position of the measuring unit in the pulse measuring method of FIG. 5, and FIG. 11 is a view illustrating the operations of FIGS. 8 through 10 sequentially.

Referring to FIG. 5, the pulse measuring method of the pulse measuring device 100 according to an embodiment of the present invention may include operation S100 of indicating a pulse position P on a surface of the skin, operation S200 of setting an initial position of the measuring unit 130 with respect to the pulse position P to match the pulse position P and positions of lights emitted from the light emitting portions 138 provided at the measuring unit 130, operation S300 of moving the measuring unit 130 by driving the movement unit 110 to dispose the pulse diagnosis sensor 131 to be in contact with the pulse position P, and operation S400 of readjusting a position of the measuring unit 130 to enable the measuring unit 130 to pressurize the surface of the skin in a vertical direction by spherically moving the measuring unit 130 with 3 DoF.

Through the foregoing operations, the mechanism as shown in FIG. 6 may operate. As shown in the left image of FIG. 6, the pulse diagnosis sensor 131 of the measuring unit 130 may be disposed accurately to be in contact with the pulse position P of the skin. As shown in the right image of FIG. 6, the position of the measuring unit 130 may be adjusted to match a pressurization direction of the measuring unit 130 and a vertical direction with respect to the pulse position P, for example, to match $Z_1$ and $Z'_1$ by operating the spherical movement portion 160.

As shown in FIG. 7, in operation S100, the pulse position P may be indicated on the surface of the skin, and the measuring unit 130 may be disposed above the pulse position P. However, in this example, the pulse position P and the position of the measuring unit 130 may be mismatched. Such mismatching may be solved by light emitting operations of the light emitting portions 138.

As shown in FIG. 8, in operation S200, the measuring unit 130 may be moved by driving the movement unit 110. In this example, laser beams may be emitted from the pair of light emitting portions 138 to match the laser beams and the pulse position P. In operation S200, the measuring unit 130 may be moved to dispose the pulse diagnosis sensor 131 vertically above the pulse position P. In this example, photographing of the photographing unit 120 of FIG. 1 may be performed simultaneously. Through the photographing, whether the pulse position P and the laser beams match may be verified.

As shown in FIG. 9, in operation S300, the measuring unit 130 may be moved downward by linearly moving the movement unit 110 with 3 DoF to dispose the pulse diagnosis sensor 131 of the measuring unit 130 to be in contact with the pulse position P. The sensor portion 150 of the measuring unit 130 may have a structure rotatable with respect to the connecting bar 141. Thus, in operation S300, the sensor portion 150 may perform a tilt motion suitable for the surface of the skin including the pulse position P. In this example, the tilting sensor 153 may measure a gradient of the pulse diagnosis sensor 131 with respect to the surface of the skin.

As shown in FIG. 10, in operation S400, a tilting angle of the unit body 133 may be adjusted based on a tilting angle of the sensor portion 150 by driving the spherical movement portion 160. In addition, the sensor housing 150 having a joint structure may be bent, and the joint members 142 of the connecting portion 140 may be bent, whereby the measuring unit 130 may efficiently pressurize the pulse position P in a vertical direction. Thus, a slip of the measuring unit 130 with respect to the surface of the skin may be prevented, and excessive pressurization may also be prevented.

In summary, as shown in FIG. 11, by driving the movement unit 110 and the measuring unit 130, the pulse diagnosis sensor 131 of the measuring unit 130 may be disposed accurately above the pulse position P. By measuring the gradient of the tilting sensor 153, the position of the measuring unit 130 may be readjusted in a vertical direction with respect to the surface of the skin including the pulse position P. However, in this example, to efficiently perform a pressurization motion in a vertical direction, for example, a direction of an arrow A, a partial bending motion of the measuring unit 130 partially having a joint structure may be performed.

As described above, according to an embodiment of the present invention, the position of the measuring unit 130 including the pulse diagnosis sensor 131 may be adjusted to a precise pulse position P by linearly moving the movement unit 110 with 3 DoF and spherically moving the measuring unit 130 with 3 DoF. Further, the measuring unit 130 may be disposed to pressurize the surface of the skin including the pulse position P in a vertical direction, whereby a pulse diagnosis may be performed accurately.

In addition, a slip of the measuring unit 130 with respect to the skin may be prevented by enabling the measuring unit 130 to pressurize the skin including the pulse position P in a vertical direction, and excessive pain to an examinee may also be prevented through appropriate pressurization.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

INDUSTRIAL APPLICABILITY

Disclosed in the specification.

The invention claimed is:

1. A pulse measuring device comprising:
   a measuring unit configured to move spherically with multiple degrees of freedom; and
   a movement unit on which the measuring unit is provided, the movement unit comprising a spherical movement portion configured to spherically move the measuring unit with multiple degrees of freedom while having a linear movement structure to linearly move the measuring unit with multiple degrees of freedom,
   wherein the measuring unit comprises:
      a unit body rotatably connected to one end portion of the movement unit;
      a connecting portion connected to a lower end portion of the unit body, and configured to rotate with respect to the unit body; and
      a sensor portion rotatably connected to the connecting portion, the sensor portion comprising a pulse diagnosis sensor,
   wherein, when the pulse diagnosis sensor is adapted to be in contact with a pulse position, a position of the measuring unit is adjusted to enable the measuring unit to pressurize the pulse position in a vertical direction by spherically moving the measuring unit with multiple degrees of freedom using the spherical movement portion, and
   wherein the unit body comprises:
      a body member;
      a pair of parallel members disposed to be parallel from the body member toward a lower side; and
      a pair of extending members configured to extend from the body member toward both sides,
      wherein the connecting portion is rotatably connected to the pair of parallel members.

2. The pulse measuring device of claim 1, wherein the measuring unit is configured to move spherically with three degrees of freedom, and the movement unit is configured to move linearly with three degrees of freedom.

3. The pulse measuring device of claim 1, wherein a pair of light emitting portions are disposed at the pair of extending members to emit lights toward a skin, respectively, and
   an initial position of the measuring unit is set by matching the pulse position and the pair of lights emitted from the pair of light emitting portions.

4. The pulse measuring device of claim 1, wherein the connecting portion comprises:
   a connecting bar to which the sensor portion is rotatably connected; and
   a pair of joint members connected to both sides of the connecting bar, respectively, and connected to the pair of parallel members, respectively, the pair of joint members comprising two joints configured to enable the pair of joint members to perform bending motions with respect to the pair of parallel members.

5. The pulse measuring device of claim 1, wherein the sensor portion comprises:

a sensor housing tiltably connected to the connecting portion, the sensor housing on which the pulse diagnosis sensor is provided at a lower end portion; and a tilting sensor configured to measure a gradient of the pulse diagnosis sensor with respect to the pulse position.

6. The pulse measuring device of claim 5, wherein the sensor housing comprises:

a first joint portion tiltably connected to the connecting portion; and a second joint portion linked to the first joint portion, wherein, when adjusting the position of the measuring unit to enable the measuring unit to pressurize the pulse position in the vertical direction, the second joint portion is configured to perform a bending motion with respect to the first joint portion.

7. The pulse measuring device of claim 1, wherein the movement unit comprises:

a supporting frame supported on a supporting surface, the supporting frame comprising a first rail;

a first movement frame configured to move linearly along the first rail in one direction, the first movement frame comprising a second rail in a direction perpendicular to the one direction;

a second movement frame configured to move linearly along the second rail, the second movement frame comprising a third rail in a vertical direction; and a third movement frame configured to move linearly along the third rail in the vertical direction, the third movement frame with one end portion at which the spherical movement portion is provided.

8. The pulse measuring device of claim 1, wherein the spherical movement portion comprises a pair of link members having a joint structure enabling a bending motion, the pair of link members configured to spherically move the measuring unit with three degrees of freedom based on the bending motion.

9. The pulse measuring device of claim 1, further comprising:

a photographing unit configured to photograph a position of the pulse diagnosis sensor with respect to the pulse position; and a processing unit configured to receive and process pulse diagnosis information obtained by the pulse diagnosis sensor.

10. A pulse measuring method of a pulse measuring device comprising a measuring unit comprising a pulse diagnosis sensor configured to sense a pulse wave at a pulse position of a skin and a unit body comprising a body member, a pair of parallel members disposed to be parallel from the body member toward a lower side, and a pair of extending members configured to extend from the body member toward both sides, the measuring unit configured to move spherically with multiple degrees of freedom; and a movement unit on which the measuring unit is provided, the movement unit comprising a spherical movement portion configured to spherically move the measuring unit with multiple degrees of freedom while having a linear movement structure to linearly move the measuring unit with multiple degrees of freedom, the method comprising:

indicating a pulse position on a surface of the skin;

setting an initial position of the measuring unit with respect to the pulse position to match the pulse position and a position of a light emitted from a light emitting portion provided in the measuring unit;

moving the measuring unit to dispose the pulse diagnosis sensor to be in contact with the pulse position by linearly moving the movement unit with multiple degrees of freedom; and readjusting a position of the measuring unit to enable the measuring unit to pressurize the surface of the skin including the pulse position in a vertical direction by spherically moving the measuring unit with multiple degrees of freedom using the spherical movement portion.

11. The method of claim 10, wherein the readjusting comprises:

measuring a gradient of the pulse diagnosis sensor with respect to the surface of the skin; and adjusting a pressurization direction of the measuring unit to match the pressurization direction and the measured gradient.

12. The method of claim 10, wherein the measuring unit comprises a unit body rotatably connected to the movement unit, a connecting portion configured to rotate with respect to the unit body, and a sensor portion configured to tilt with respect to the connecting portion, the sensor portion comprising the pulse diagnosis sensor, and the adjusting comprises tilting the sensor portion with respect to the connecting portion to dispose the pulse diagnosis sensor to be in surface contact with the surface of the skin, bending the connecting portion, and matching an axial direction of the unit body and an axial direction of the sensor portion.

13. The method of claim 10, wherein the setting comprises performing photographing using a photographing unit provided in the pulse measuring device to verify whether the pulse position and the position of the light emitted from the light emitting portion match.

* * * * *